United States Patent
Lezdey et al.

(10) Patent No.: US 6,511,960 B2
(45) Date of Patent: Jan. 28, 2003

(54) CROMOLYN FOR EYE AND EAR INFECTIONS

(75) Inventors: John Lezdey, Indian Rocks Beach, FL (US); K. Anne Kronis, Tampa, FL (US); Darren Lezdey, Indian Rocks Beach, FL (US)

(73) Assignee: Alphamed Pharmaceuticals Corp, Clearwater, FL (US)

( * ) Notice: Subject to any disclaimer, the term of this patent is extended or adjusted under 35 U.S.C. 154(b) by 34 days.

(21) Appl. No.: 09/756,618

(22) Filed: Jan. 5, 2001

(65) Prior Publication Data

US 2002/0091100 A1 Jul. 11, 2002

(51) Int. Cl.$^7$ .......................... A61K 38/16; A61K 31/70
(52) U.S. Cl. ................. 514/8; 514/12; 514/21; 514/54

(58) Field of Search .................. 514/8, 12, 21, 514/54

(56) References Cited

U.S. PATENT DOCUMENTS 5,190,917 A * 3/1993 Lezdey et al. ................ 514/12

* cited by examiner

*Primary Examiner*—Elli Peselev
(74) *Attorney, Agent, or Firm*—John Lezdey

(57) ABSTRACT

The present invention provides a method and composition for treating eye and ear inflammation and eye and ear infections. The compositions contain a cromolyn compound alone or in combination with a corticosteroid. A steroidal antiphlogistic compound, a non-steroidal antiphlogistic compound and optionally hyaluronic acid may be added.

12 Claims, No Drawings

CROMOLYN FOR EYE AND EAR INFECTIONS

FIELD OF THE INVENTION

The present invention relates to a method of treating eye and ear infections including those resulting from parasites and/or infections characterized by the presence of inflammation, increased kallikrein and kinin activity. More particularly, there is provided compositions containing a cromolyn compound alone or in combination with a corticosteroid.

BACKGROUND OF THE INVENTION

Aracadonic acid is liberated in damaged, wounded, or inflamed tissues from phospholipids of cytoplasmatic membranes by the action of phospholipase enzyme and may be then metabolized by the cyclooxygenase cycle (by lipoxygenase enzyme) to prostanoids and eicosanoids. Antiphlogistics of both the steroid and nonsteroid nature, antibiotics, and sulfonamides are often used for therapeutic purposes. The antibiotics which specifically suppress pathogenic microbes and are often used in ophthalmology, are tetracycline, chloramphenicol, bacitracin, and neomycin. Therapeutics which prevent the development of inflammation (antiphlogistics) are both steroid and nonsteroid. The steroid antiphlogistics (e.g., dexamethasone block phospholipase). The anti-inflammatory drugs of nonsteroid nature (e.g., indomethacin, flurbiprofen, pirprofen) block cyclooxygenase and others. The blockage of these enzymes is important, because the products formed in metabolic cycles have a strong chemotactic effect (they cause accumulation of leukocytes in the sites of origin), (e.g., some leucotrienes) and increase the vascular permeability. This contributes to an excess development of the inflammation. Inflammations (both of infectious and noninfectious origin) are very dangerous for the anterior and posterior segments of the eye. Thus, scars formed in the cornea during the final stage of the healing process cause the loss of an exceptional function of this tissue, i.e. transparency. The loss of transparency of optical media of the eye (cornea, lens) then leads to a reduction or even loss of sight.

A disadvantage of locally applied antiphlogistics is the relatively low efficiency, retarded healing, and contribution to the development of infection. The local effect of antibiotics is limited.

One of the very prospective possibilities of treatment is the inhibition of plasmin and other destruction proteases (e.g., collagenase or elastase) with specific inhibitors. These enzymes either directly develop the destruction processes (e.g., plasmin) or enable these processes by their own activity (e.g., collagenase, elastase). However, plasmin is effective not only as an initiator developing the degeneration processes proceeding in cascades, but also contributes to an excessive development of inflammation by several other mechanisms of which at least chemotaxis should be mentioned. U.S. Pat. Nos. 5,217,951; 5,290,762, and 5,190,917 which are herein incorporated by reference disclose the treatment of inflammation with human-type serine protease inhibitors alone or in combination with a corticosteroid. None of the references teach or suggest eye and ear infections caused by parasites or relating to Pseudomonas infection.

What is needed then is a medicamentous form for external use as an ophthalmologic or otolaryngologic drug which is readily available and can be cheaply produced.

SUMMARY OF THE INVENTION

The medicamentous form or composition of the present invention is delivered in an aqueous or ointment base particularly suited for ophthalmologic and otolaryngologic application. This medicamentous form contains a compound selected from the group consisting of cromolyn, a salt of cromolyn and derivatives or esters thereof alone or in combination with a corticosteroid. These can also be delivered with antiphlogistics and antibiotics.

Accordingly, an object of the present invention is to provide a medicamentous form having strong antiexudative, antiphlogistic and antimicrobial effects.

Still another object of the present invention is to provide a medicamentous form having therapeutic effects including the inhibition of plasmin, leucolytic elastase, serine proteases and prevents the degranulation of mast cells.

A further object of the invention is to provide a composition for treating otitis.

Another object of the present invention is to provide a medicamentous form that inhibits the activation of latent forms of some endoproteases and several further subsequent reactions of chemotaxis and vascularization of the cornea.

Yet another object of the present invention is to treat ear and eye infections characterized by the presence of inflammation.

DETAILED DESCRIPTION OF THE PREFERRED EMBODIMENT

The composition of the present invention is a medicamentous form or composition in an aqueous or ointment base particularly suitable for ophthalmologic and otolaryngologic application. The medicamentous form contains a cromolyn compound, preferably, cromolyn sodium, disodium cromolyn or the esters thereof alone or in combination with a corticosteroid. These cromolyn compounds are applied either individually or in combination with a corticosteroid after being dissolved in physiological saline or buffer solution with a pH of 6.5 to 7.5, which is advantageously ionically balanced (e.g., phosphate or borax buffer) or present in the ointment base.

The ionically balanced buffer solution means that sodium chloride is added to the buffer solution in such a way that the resulting solution is ionically balanced. For example, the precise performance for borax buffer with pH 7.4 is as follows:

Solution A—1.9 g $Na_2P_4O_7$ per 100 ml $H_2O$ pro injection.
Solution B—1.25 g $H_3BO_3$+0.3 g NaCl per 100 ml $H_2O$ pro injection. Cromolyn sodium alone provides a mix of 10 ml of solution A+90 ml of solution B.

The medicamentous form according to the preferred embodiment in the liquid state may further advantageously contain 0.05 to 15 percent by weight of thickeners selected from the group comprising hydroxypropylmethyl cellulose, methyl cellulose, polyvinylpyrrolidone, polyvinyl alcohol, poly (alkaline glycols), polyhydroxyalkyl, (meth)acrylates or poly(meth)acrylamides for use especially in ear infections.

Concentrations of the cromolyn compound when locally applied, act not only curably in the advanced stage of disease but also prospectively by the prevention of the formation of destructive processes if timely administered. The vehicles or thickeners with protracted effect then enable a longer contact of the remedy with the tissues.

The medicamentous form according to the preferred embodiment may contain 0.05 to 1.5 percent by weight of steroidal antiphlogistics such as indomethacin or 0.2 to 1 percent by weight of antibiotics such as bacitracin, neomycin, tetracycline, or chloramphenicol and/or hyaluronic acid. A corticosteroid is synergistic with the cromolyn compound in reducing inflammation.

The combination of the cromolyn compound with antiphlogistics or antibiotics, or all substances together, increases the antiinflammatory and anti-microbial effect because the inhibitors block some products of microbes such as elastase or other proteases. This enables one to use the antibiotics only locally and in smaller doses. The concentration of antiphlogistics may be reduced and, at the same time, the therapeutic effect is higher and the time of treatment shorter which is of great value in healing of tissue.

The corticosteroid is generally less than 1% by weight of composition, preferably about 0.25 to 0.5% by weight. The cromolyn compound is generally about 0.1 to 2% by weight of the composition. Greater amounts of the cromolyn compound can be used when administered alone.

Ear infections are generally characterized by the presence of pseudomonas and increased tissue kallikrein and kinin activity which causes the inflammation as a result of mast cell degranulation. The more serious the infection, the greater the levels of pseudomoas, kallikrein activity and elastase. The reduction of inflammation, especially kallikrein and kinin activity also results in reduction of pain.

Parasitic infestation of the eyes and ears has resulted in increased kallikrein activity and protease levels which are released by the parasites. The common parasites which invade the eyes and ears usually through contaminated water generally express serine proteases. The protozoan parasite Cryptosporidium parvum, for example, expresses a protease-like component which is recognized by the cromolyn compound.

Shistosomiasis infections are easily started by Shistosoma mansoni entering the eyes and ears of swimmers to cause an inflammatory response.

Hyaluronic acid promotes healing and is especially advantageous in treating injury to the cornea.

The medicamentous form is most often applied by instillation or as an ointment into the conjunctival sac. However, it can also be used for irrigation or lubrication of the eye, facial sinuses, and external auditory meatus. It may also be injected into the anterior eye chamber and other places. The medicamentous form in the liquid state may be also present in a hydrophilic three-dimensional polymer matrix in the form of a strip, contact lens, and the like from which the active components are released. The incorporation of medicamentous form into a hydrophilic matrix can be performed according to the invention by conditioning of the matrix in the solution of medicamentous form in order to obtain the required concentration of the cromolyn compound and also for the antiphlogistics and antibiotics in the polymer matrix.

The invention is illustrated in the examples of performance and the examples are provided without the intention of limiting the scope of the present invention.

The preparation of medicamentous form in liquid state is begun by separately dissolving each substance in a small amount (10 to 40 ml) of buffer or physiological saline.

The ointment base is prepared by melting 10 g lanolin, 10 g liquid paraffin, and 80 g white vaseline in bath water. The mixture is then strained through a hydrophilic gauze and sterilized. If the applicable therapeutic is easily soluble in water, it is dissolved in the necessary amount of distilled water for the preparation of injections, mixed with the ointment base in part melted in a water bath and stirred until completely cooled. If the therapeutic is insoluble in water, it is used for the preparation in the finest powdered form. However, it is first titrated in a smaller amount of liquid paraffin and then mixed with the ointment base.

The corticosteroids which can be used in the treatment of the diseases include triamcinolone acetonide, fluoroandrenolide, prednisone, beclomethasone valerate, amcinolone, dexamethasone, betamethasone valerate, halocinonide, clocortolone hydrocortisone valerate, hydrocortisone acetate and the like.

The following examples further illustrate the practice of this invention, but are not intended to be limiting thereof. It will be appreciated that the selection of actual amounts of specific cromolyn compound and corticosteroid to be administered to any individual patient will fall within the discretion of the attending physician and will depend on the patient's age, and severity of disease.

EXAMPLE 1

A mixture is provided by combining cromolyn sodium 1 g; hydroxypropyl methyl cellulose 1 g; and ionically balanced borax buffer of pH 7.4 up to 100 g. Drops of this composition dosed into the conjunctival sac of a patient at intervals of 3 hours heals allergic conjunctivitis within 3 to 5 days.

If desired, about 0.5 g of dexamethasone can be added to the composition.

EXAMPLE 2

A mixture is provided by combining cromolyn disodium 0.005 g; hydroxypropyl methyl cellulose 2.5 g; and tonically balanced phosphate buffer of pH 7.4 up to 100 g. The drops were dosed into the ear of a patient with swimmer's ear three times a day. Pain was reduced with the initial dose.

EXAMPLE 3

A mixture is prepared by combining cromolyn sodium 0.005 g; polyvinylalcohol 0.001 g; 0.00 g of hyaluronic acid and ionically balanced borax buffer of pH 7.4 up to 100 g. Drops of the mixture were applied into the conjunctival sac of the patient at intervals of 2 hours. This heals minute wounds of the conjunctive, cornea, and eyelids within 4 days.

EXAMPLE 4

A mixture is prepared by combining cromolyn sodium 0.2 g; hydroxypropyl methyl cellulose 2.5 g; and physiological saline up to 100 g. An etched and burnt cornea can be healed during 4 days by application of the drops four times a day. The transparency of the cornea can be recovered either completely or at least in the periphery of the cornea.

EXAMPLE 5

A mixture is prepared combining cromolyn sodium 0.01 g; dexamethasone sodium phosphate 0.1 g; hydroxypropyl methyl cellulose 2.5 g; and ionically balanced borax buffer up to 100 g. The eye drops can be used to heal severe allergic conjunctivitis by instillation three times a day.

EXAMPLE 6

A mixture is prepared by combining cromolyn sodium 0.1 g; dexamethasone sodium phosphate 0.5 g; hydroxypropyl methyl cellulose 2 g; 0.58 g hyaluronic acid and ionically balanced phosphate buffer up to 100 g. The drops can be administered into an infected ear 3 times a day. Pain and inflammation will be reduced immediately.

EXAMPLE 7

A mixture is prepared by combining 1.0 g of cromolyn sodium; 0.05 g of hyaluronic acid; dexamethasone sodium phosphate 0.1 g; chloramphenicol 0.5 g and physiological saline up to 100 g. The solution can be used in the treatment of rhinal allergoses and allergoses of meatus acusticus externus.

What is claimed is:

1. The method for treating optic and optic infections resulting in inflammation and kalligrein activity by the parasites and microbes, which comprises administering to the site of the infection an effective amount of a cromolyn compound selected from the group consisting of cromolyn, cromolyn salts, esters and derivatices of cromolyn in a suitable pharmaceuticaly acceptable carrier.

2. The method of claim 1 wherein said cromolyn compound is cromolyn sodium.

3. The method of claim 1 including a corticosteroid.

4. The method of claim 3 wherein said corticosteroid is selected from the group consisting of hydrocortisone acetate, dexamethasone, betamethasone and triamcinolone acetonide.

5. The method of claim 1 wherein said inflammation is caused by parasites.

6. The method of claim 1 including hyaluronic acid.

7. The method of claim 1 including an effective amount of an antibiotic.

8. The method of claim 7 wherein said antibiotic is antipseudomones.

9. The method of claim 1 including a bradykinin antagonist.

10. A method for treating optic infection characterized by elevated pseudomonas and kallikrein activity which comprises administering cromolyn sodium to the site of infection in a suitable pharmaceutical carrier.

11. A method for treating optic and optic inflammation caused by parasites which comprises administering an effective amount of a cromolyn compound and a corticosteroid to the site of inflammation in a suitable pharmaceutical carrier.

12. A composition for opthamalogic or otolaryngologic application for patients suffering from parasitic infestation or inflammation characterized by the presence of pseudomonas and increased kallikrein and kinin activity which comprises:

a) about 0.1% to 2% by weight of a cromolyn compound selected from the group consisting of cromolyn sodium, cromolyn disodium, and the esters thereof;

b) about 0.25 to 0.5 percent by weight of a corticosteroid;

c) about 0.05 to 1.5 percent by weight of a steroidal antiphlogistic compound;

d) about 0.05 to 1.5 percent by weight of hyaluronic acid, in an aqueous pharmaceutically acceptable base.

* * * * *

UNITED STATES PATENT AND TRADEMARK OFFICE
CERTIFICATE OF CORRECTION

PATENT NO. : 6,511,960 B2
DATED : January 28, 2003
INVENTOR(S) : Lezdey et al.

It is certified that error appears in the above-identified patent and that said Letters Patent is hereby corrected as shown below:

Column 1,
Line 14, change "aracadonic" to -- arachadonic --

Column 3,
Line 24, change "pseudomoas" to -- pseudomonas --

Column 5,
Line 9, change the first instance of "optic" to -- otic --
Line 15, change "derivatices" to -- derivatives --

Column 6,
Line 2, change "antipseudomones" to -- antipseudomonas --
Line 9, change the first instance of "optic" to -- otic --

Signed and Sealed this

Eighteenth Day of November, 2003

JAMES E. ROGAN
*Director of the United States Patent and Trademark Office*